United States Patent [19]

Herrmann et al.

[11] Patent Number: 5,219,760

[45] Date of Patent: Jun. 15, 1993

[54] PROCESS FOR THE DETERMINATION OF IRON

[75] Inventors: Uwe Herrmann, Bernried; Jürgen Ruhm, Werl, both of Fed. Rep. of Germany

[73] Assignee: Boehringer Mannheim GmbH, Mannheim, Fed. Rep. of Germany

[21] Appl. No.: 750,766

[22] Filed: Aug. 22, 1991

Related U.S. Application Data

[63] Continuation of Ser. No. 355,568, May 23, 1989, abandoned.

[30] Foreign Application Priority Data

May 26, 1988 [DE] Fed. Rep. of Germany ....... 3817907

[51] Int. Cl.$^5$ ............................................. G01N 33/20
[52] U.S. Cl. ........................................ 436/84; 436/74; 436/166; 436/910
[58] Field of Search ............... 436/74, 84, 166, 63, 436/910

[56] References Cited

U.S. PATENT DOCUMENTS

| | | | |
|---|---|---|---|
| 3,506,404 | 4/1970 | Evans | 436/74 |
| 3,537,822 | 11/1970 | O'Malley | 436/74 |
| 4,579,825 | 4/1986 | Siedel et al. | |
| 4,703,015 | 10/1987 | Tabacco et al. | 436/74 |
| 4,708,939 | 11/1987 | Siedel et al. | |
| 4,810,656 | 3/1989 | Torelli | 436/74 |
| 4,961,970 | 10/1990 | Siedel et al. | 436/74 |

FOREIGN PATENT DOCUMENTS 228060 7/1987 European Pat. Off. .

OTHER PUBLICATIONS

Clin. Chem. (1980) 26:327–331.
Clin. Chem. (1977) 23:237–240.
La Recerca Clin. Lab. (1986) 16:523–532.
C. Tanford, Adv. Prot. Chem. (1986) 23:121 ff 159, 173, and 182–186.
Clin. Biochem. (1981) 14:311–315.
Biological Abstracts, vol. 83, 1987, 53572.
Patent Abstracts of Japan, Dec. 2, 1983, 58148964(A).

*Primary Examiner*—Lyle Alexander
*Attorney, Agent, or Firm*—Felfe & Lynch

[57] ABSTRACT

To determine iron in serum by the release of bound iron and reduction of the released iron to $Fe^{2+}$, a first solution of a denaturing agent at a concentration of 1 to 8 mol/l is added to the serum, then a second solution is added which contains the colour reagent and likewise a denaturing agent at a concentration of 1 to 8 mol/l and subsequently the colored complex is measured photometrically.

8 Claims, 2 Drawing Sheets

PROCESS FOR THE DETERMINATION OF IRON

This application is a continuation of application Ser. No. 07/355,568, filed May 23, 1989 now abandoned.

BACKGROUND OF THE INVENTION

The invention concerns a process for the determination of iron in body fluids by release of the bound iron, reduction to $Fe^{2+}$, addition of a chromogenic system suitable for the detection of iron and measurement of the complex with chromogen. The invention also concerns a reagent combination which is suitable for the measurement of lipaemic sera even without addition of mixtures of detergents to remove turbidity.

Disorders of iron metabolism, especially iron deficiency and disturbances in iron resorption, occur particularly commonly in the female population. Therefore, the determination of iron in body fluids, especially in serum, is one of the standard determinations in medical analysis. Iron is supplied with the food and is absorbed across the mucous membrane of the intestine. It is then transported, bound to transferrin in a trivalent state, to the bone marrow where it is mainly incorporated into haemoglobin. Absorption of too little iron can lead to anaemic symptoms.

The determination of iron in serum is one of the most frequently performed trace element analyses in clinical diagnosis. Various processes are known for this purpose. Thus in Clin. Chem. 26, (1980) 327-331 a process is described in which trivalent iron bound to transferrin in the form of a carbonate complex is released in a strongly acid medium. A disadvantage of this process is that the strongly acid reagents are caustic and corrosive. In order to overcome this disadvantage, it is known for example from Clin. Chem. 23, (1977) 237-240 and from Z. Klin. Chem. 3 (1965) 96-99 that protein denaturing agents such as concentrated guanidinium chloride or anionic detergents can be used to release the iron.

In the known embodiments of these processes errors in measurement occur when iron is determined in turbid lipaemic sera. Neither guanidinium chloride nor the anionic detergents have a sufficient clarification power to achieve a complete elimination of the turbidity.

In order to solve this problem the use of a mixture of non-ionic and anionic detergents to release the iron in a weakly acid medium was suggested in EP 130 537. However, it was found that, although the employment of these detergents results in a rapid and complete clarification of lipaemic sera, in sera with a high immunoglobulin content (gammopathy sera) an increase in turbidity is observed which can falsify the results of the measurements. Furthermore, the recovery of iron in strongly haemolytic sera is not completely satisfactory.

In addition, in all processes known up to now, a detergent must always be present either as denaturing agent or in order to avoid turbidity or to avoid interactions between chromogen and the sample. The presence of detergents is, however, disadvantageous in particular in the application of the methods on automatic analysers since detergents cause the formation of foam and can thereby considerably interfere with the measurements.

SUMMARY OF THE INVENTION

The object of the present invention was therefore to provide a process and a reagent for the determination of iron in serum in which, on the one hand, aggressive constituents do not have to be used and, on the other hand, interference by lipaemic sera is avoided, without the measurement being disturbed by haemolytic samples or by sera with increased immunoglobulin contents.

Furthermore, in order to facilitate automation and for purposes of simplification, it is desirable that the process works without foam-producing detergents and that no preceding deproteinization is necessary.

Thus in accordance with the present invention there is provided a process for the determination of iron in serum by addition of a protein-denaturing agent to release bound iron, reduction of the released iron to $Fe^{2+}$, addition of a colour reagent solution and photometric measurement of the formation of the coloured complex, wherein a first solution of a denaturing agent is added to the serum at a concentration between 1 and 8 mol/l, after which a second solution is added containing the colour reagent and likewise a denaturing agent at a concentration of 1 to 8 mol/l and then the coloured complex is measured.

The present invention is based on the observation that one can also assay in the absence of detergents when a two-step procedure (first step: displacement of the iron from the binding proteins with a denaturing agent, second step: colour reaction) is used in which the formation of turbidity in the solution on addition of the colour reagent can be avoided if denaturing agents are also added to the colour reagent. By these means the measurement of lipaemic sera free of interference is possible.

Various protein denaturing agents are known which can be added to displace the iron from binding proteins in particular from transferrin. Apart from detergents, a multitude of salts have been used for this purpose, as for example guanidinium chloride or guanidinium acetate, magnesium sulphate (K.Lauber, Z. Klin. Chem. 3, 1965, 96-99), magnesium chloride (G. Brivio, La Ricerca Clin. Lab. 16, 1986, 523-532) and NaCl (EPA 0228060). In the 1 known procedures for determining iron in a two-step process with a prior denaturation step and subsequent colour reaction the ionic strength of the denaturing reagent is lowered by the addition of the colour reagent. Surprisingly, it emerged that this alteration of the ionic strength was responsible for the error in measurement of lipaemic sera in the iron test.

It is assumed that firstly, iron is released from its carrier proteins by the denaturing agent and that, secondly, a definite level of turbidity establishes in lipaemic sera. It is therefore preferable to measure the turbidity before addition of the colour reagent and to deduct it as a sample blank. Since, according to the present invention the colour reagent contains either only a slightly different or preferably the same concentration of denaturing agent as in the denaturing solution, the background turbidity remains unaffected during formation of the chromogen complex.

In general apart from the examples mentioned above, high concentrations of the protein denaturing agents cited by C. Tanford in Adv. Prot. Chem. 23, on pages 121 ff., and in particular on pages 159, 173, 182-186, 1986, are suitable for protein denaturation within the scope of the present invention, whereby as cations: alkaline or alkaline-earth cations, substituted or unsubstituted ammonium compounds or other organic cations such as e.g. guanidinium and as anions: halides, sulphates, perchlorates, thiocyanates or other inorganic or also organic anions e.g. acylate (as for example acetate)

or heparinate are possible. Preferred reagents for the denaturation of iron-binding proteins are urea as well as salts of the cations magnesium$^{2+}$ and guanidinium, particularly preferred are the salts of the guanidinium cation such as chloride, acetate, thiocyanate or sulphate.

DESCRIPTION OF THE PREFERRED EMBODIMENT

Figure 1:
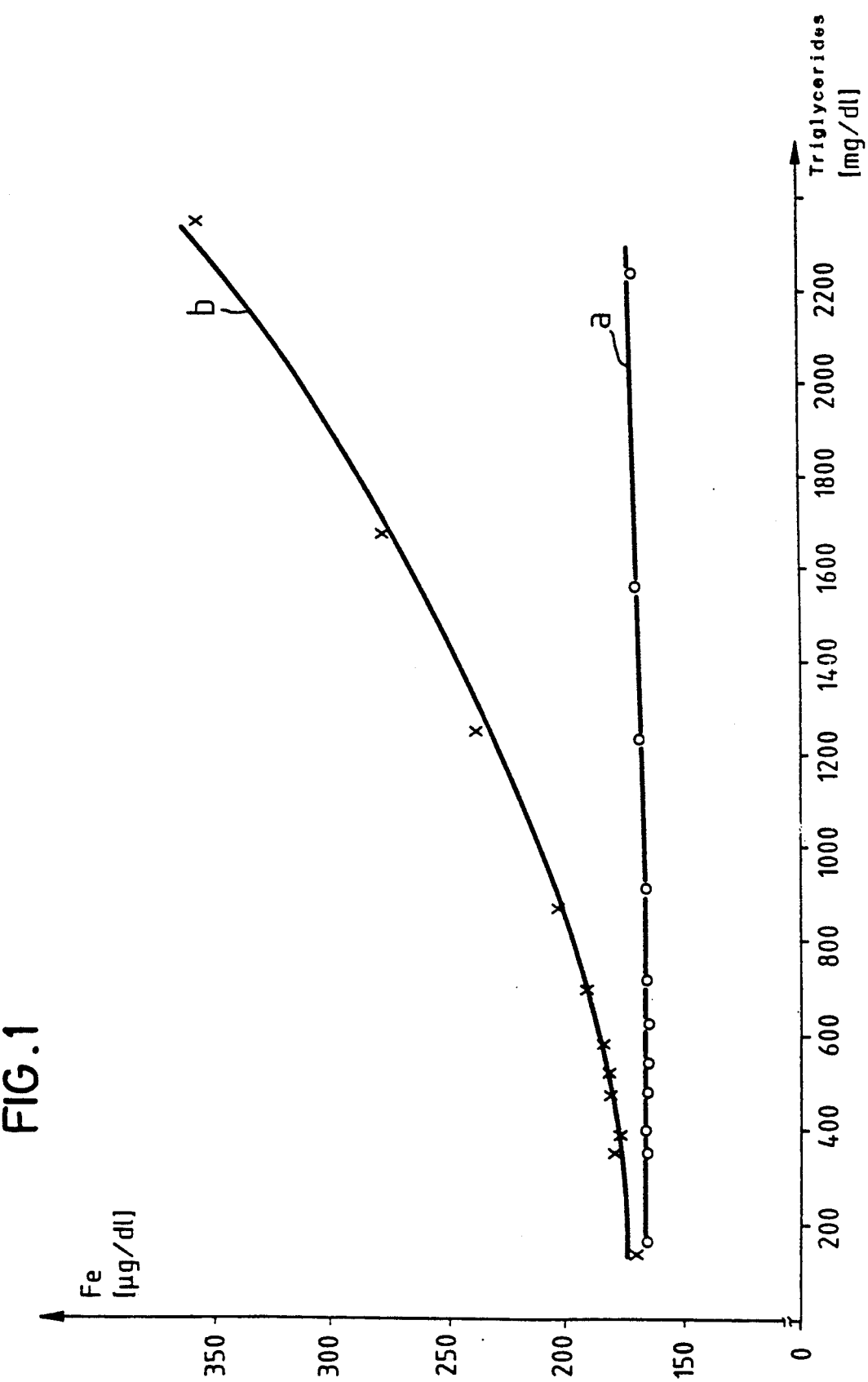
FIG. 1 represents the amount of iron recovered vs. the triglyceride content of the serum.

The concentration of the denaturing agent in both solutions of the iron test according to the present invention must be relatively high and between 1 and 8 mol/l. Best results are obtained with concentrations between 4 and 6 mol/l. At concentrations below 1 mol/l the displacement of the iron from transferrin becomes increasingly slower. For the particularly preferred guanidinium chloride, the preferred concentration range is between 1 and 6 mol/l, concentrations between 4 and 5 mol/l are especially preferred.

A large degree of correspondence between the concentrations of the denaturing agents in both solutions is particularly advantageous. If the said concentration is less in the colour reagent than in the pre-incubation solution, then it is possible that on addition of the colour reagent to samples of lipaemic sera a recurrence of the turbidity occurs which simulates a higher iron content of the samples. In the opposite case, in which the denaturing agent is at a higher concentration in the colour reagent, a subsequent additional clarification can occur and this would result in an iron measurement which is too low. Therefore the concentration of the denaturing agent in the preincubation reagent and colour reagent should preferably differ by less than 20%, especially preferred are differences of less than 5%.

To perform the process according to the present invention, the sample solution is buffered in a weakly acid range; the range between pH 4 and 6 being especially preferred. Compounds suitable for the buffering agent are those which have a pK-value from 4 to 6 and which do not complex iron. Examples of suitable compounds are: acetate buffer, phosphate buffer, succinate buffer and Tris-buffer.

Acetate buffer is used as the preferred buffering agent. The buffer is preferably used in a concentration of from 20 to 500 mmol/l, especially preferred are concentrations between 50 and 150 mmol/l.

For the determination of iron, a reducing agent such as ascorbic acid or dithionite is then added in accordance with known methods in order to reduce the released iron, present in a trivalent form, into the divalent form. The reducing agent is preferably added to the first solution. In addition, a suitable chromogenic system is added for the detection of iron. Such chromogenic systems are described for example in EP 228060, Clin. Biochem. 14 (1981) 311–315 and Clin. Chem. 23 (1979) 237–240. Particularly suitable are complexing agents of the ferroin type which yield a colour when complexed with iron that can be measured photometrically. Examples of suitable substances are bathophenanthroline and the disodium salt of 3'(2'-pyridyl)-5,6-diphenyl-1,2,4-triazine-sulphonic acid. The formation of the coloured complex is proportional to the amount of iron present in the sample and can be measured photometrically according to known methods.

A further embodiment of the present invention is a combination of reagents for the determination of iron in serum characterized by a first reagent containing:

| |
|---|
| 20 to 500 mmol/l buffering agent, pH 4 to 6 |
| 1 to 8 mol/l denaturing agent and |
| 0.1 to 100 mmol/l reducing agent | and separate from this a second reagent, containing:

| |
|---|
| 20 to 500 mmol/l buffering agent, pH 4 to 6 |
| 1 to 8 mol/l denaturing agent and |
| 0.5 to 50 mmol/l chromogen | in the form of aqueous solutions or suitable dry mixtures for their production.

Reagent 1 preferably contains:

| |
|---|
| 5 to 50 mmol/l reducing agent |
| 4 to 6 mol/l denaturing agent and |
| 50 to 150 mmol/l buffer | and Reagent 2 contains:

| |
|---|
| 4 to 6 mol/l denaturing agent |
| 50 to 150 mmol/l buffer and |
| 1 to 20 mmol/l chromogen |

The following examples elucidate the invention in more detail.

EXAMPLE 1

The following reagents were used for the determination of iron in serum:

| Reagent 1 | |
|---|---|
| guanidinium chloride | 4.5 mol/l |
| acetate buffer pH = 5.0 | 0.15 mol/l |
| ascorbic acid | 0.023 mol/l |
| Reagent 2 | |
| guanidinium chloride | 4.5 mol/l |
| acetate buffer pH = 5.5 | 0.02 mol/l |
| Ferrozine$^R$ | 1.7 mmol/l |
| (3-(2-pyridyl)-5-6-diphenyl-1,2,4-triazine-sulphonic acid-disodium salt) | |

700 μl of the denaturing reagent 1 was pipetted into a cuvette containing a sample volume of 40 μl, incubated for 5 min at T=25° C. and the absorbance measured at 570 nm ($A_{1\ sample}$). Then 100 μl of the colour reagent $R_2$ was added. After a further 5 min the colour developed was measured ($A_{2\ sample}$). A reagent blank was measured before ($A_{1RB}$) and after ($A_{2RB}$) addition of the colour reagent, in which case 40 μl of twice distilled water was added instead of the sample. Accordingly, the resulting absorbance change for the iron determination may be described by the following equation:

$$\Delta A = \left( A_{2\ sample} - \left[ \frac{740}{840} \cdot A_{1\ sample} \right] \right) -$$

-continued $$\left(A_{2\,RB} - \left[\frac{740}{840} \cdot A_{1\,RB}\right]\right)$$

A control serum with a known iron content was used to calibrate the iron determination.

Samples were made by mixing a control serum of known iron content (116 μg/dl) with a very turbid fat emulsion (Intralipid$^R$), Pfrimmer & Co., Erlangen). First a series of aqueous pre-dilutions of this emulsion were prepared ranging from 1 part Intralipid +10 parts water to 1 part Intralipid +0.5 parts water which showed an increase in turbidity and an increase in the measured concentration of triglycerides (triglyceride test, measured on the Hitachi 704). An aliquot was taken from each of these pre-dilutions and mixed with 19 parts of the control serum. The results of iron recovery are plotted against the triglyceride content in FIG. 1. Curve a shows the independence of the iron recovery from turbidity using the reagent composition described above, whereas curve b shows the results with an analogous reagent composition in which guanidinium chloride has been omitted from R$_2$.

EXAMPLE 2

Figure 2A:
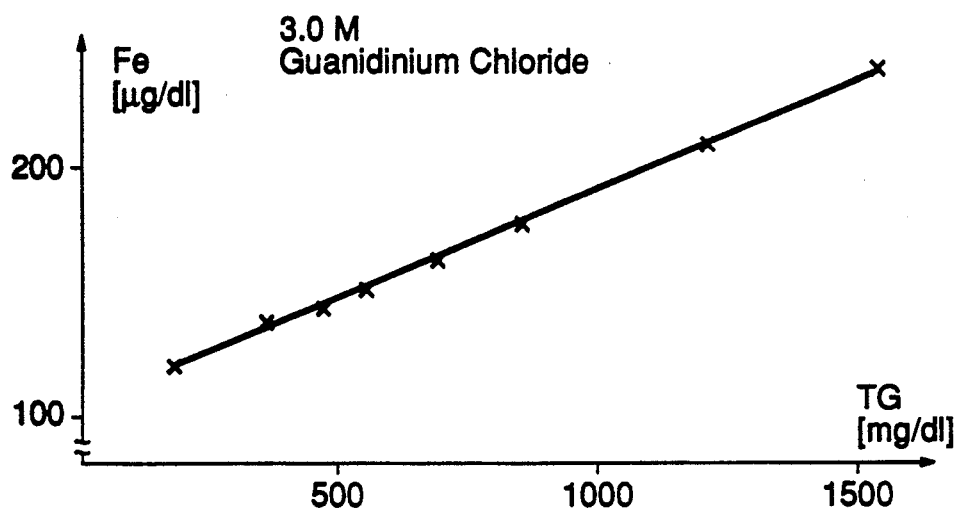
FIGS. 2(a-c) show errors in measurements correlated to the various concentrations of denaturing reagent in the second reagent.
Figure 2B:
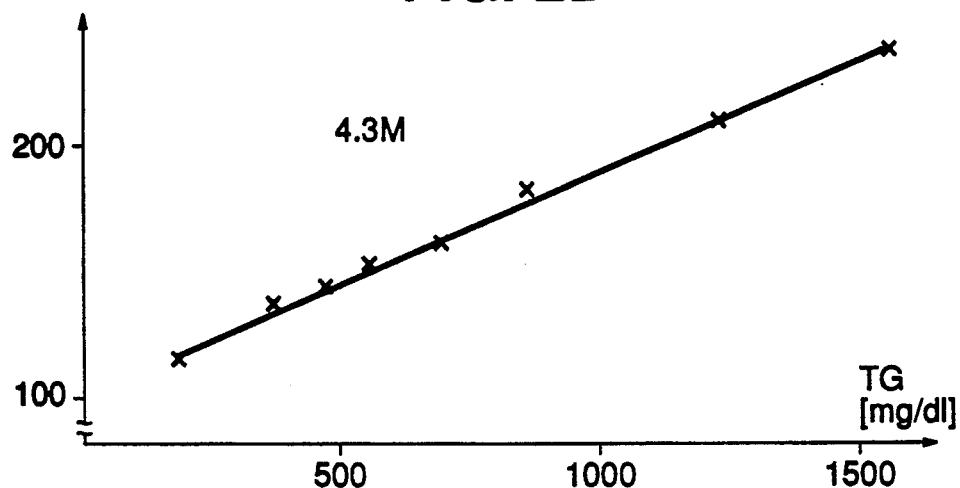
Figure 2C:
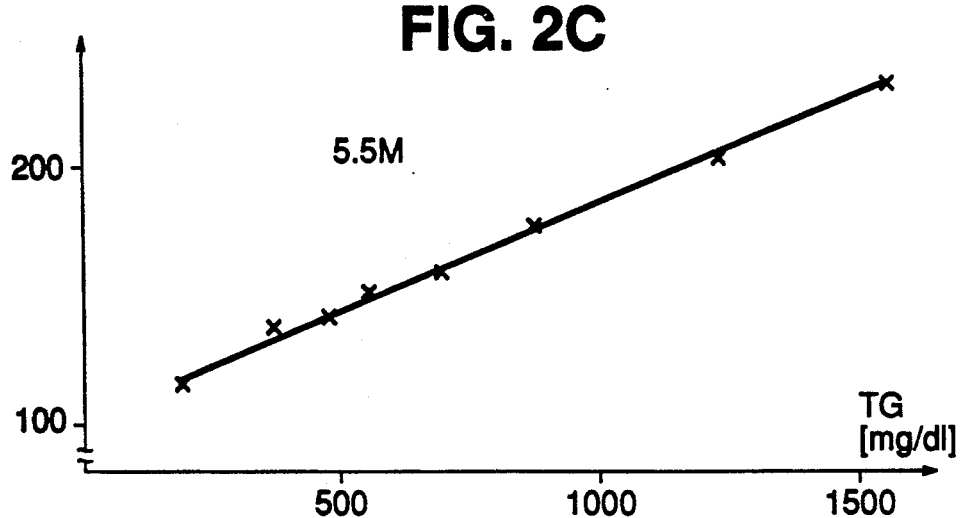

Using a measurement procedure analogous to Example 1, the concentration of the denaturing agent guanidinium chloride in R$_1$ was varied over a wide range, while no denaturing agent was added to the colour reagent. It can be seen from FIG. 2 that the error in measurement is not dependent on the concentration of the denaturing agent but rather, as shown in Example 1, on its addition to Reagent 2.

EXAMPLE 3

Using a measurement procedure analogous to Example 1, the chromogen was omitted from Reagent 2 and instead of 4.5 mol/l guanidinium chloride various other agents were used which are known to be denaturing agents. The change in turbidity of an Intralipid sample with a triglyceride concentration corresponding to the highest one used in Example 1 was measured at 570 nm. Due to the omission of the colour reagent, the turbidity change is not obscured by absorbance changes arising from iron. The relative changes in turbidity on addition of Reagent 2 are listed in Table 1:

TABLE 1

| Relative change in turbidity at 570 nm for different additions to Reagent 2 | |
|---|---|
| Addition: | ΔA570 [%] (Turbidity) |
| — | 32.1 |
| 4.5 mol/l guanidinium chloride | 2.6 |
| 3.4 mol/l sodium chloride | 20.4 |

TABLE 1-continued

| Relative change in turbidity at 570 nm for different additions to Reagent 2 | |
|---|---|
| Addition: | ΔA570 [%] (Turbidity) |
| 5 mol/l urea | 12.9 |

It is apparent that the relative change in turbidity can be greatly diminished by addition of different denaturing agents to Reagent 2.

We claim:

1. A method for the determination of iron in lipaemic serum in an automatic analyzer consisting of
    adding a first solution of a first non-detergent, non-foam forming protein denaturing agent selected from the group consisting of alkaline, alkaline-earth, substituted or unsubstituted ammonium ions or guanidium-ions as cations and halogen, sulfate, perchlorate, thiocyanate, acylate or heparinate as anions and urea to the lipaemic serum at a concentration between 1 and 8 mol/l, and at pH 4–6 to release bound iron, carrying out a turbidimetric measurement after addition of the first solution, reducing the released iron to Fe$^{2+}$,
    adding to the lipaemic serum sample a second solution containing a reagent that reacts with the released Fe to form a colored iron complex and the first or a second non-detergent, non-foam forming denaturing agent selected from the group consisting of alkaline, alkaline-earth, amine or guanidinium-ions as cations and halogen, sulfate, perchlorate, thiocyanate, acylate or heparinate as anions and urea at a concentration of 1 to 8 mol/l wherein the difference in the concentrations of the first and second reducing agents is less than 20%,
    photometrically measuring the colored complex formed, and subtracting the turbidimetric measurement from the photometric measurement to determine the quantity of iron in the serum wherein the above determination and method are carried out in an automatic analyzer without prior deproteinization.

2. The method of claim 1 wherein the difference between the concentration of the denaturing agents in the second and the first solutions is less than 5%.

3. The method of claim 1 wherein ascorbic acid or dithionite is added to reduce the iron.

4. The method of claim 1 wherein the color reagent is bathophenanthroline or the disodium salt of 3′-(2-pyridyl)-5,6-diphenyl-1,2,4-triazine-sulphonic acid.

5. The method of claim 1 wherein a turbidometic measurement is carried out after addition of the first solution and this measurement is then subtracted from that of the solution of the colored complex in order to determine the quantity of iron.

6. The method of claim 1 wherein the denaturing agent is guanidinium salt.

7. The method of claim 6 wherein the concentration of the guanidine hydrochloride is 4 to 5 mol/l.

8. The method of claim 4 wherein the concentration of buffering substance is 20 to 500 m mol/l.

* * * * *

UNITED STATES PATENT AND TRADEMARK OFFICE
CERTIFICATE OF CORRECTION

PATENT NO. : 5,219,760
DATED : June 15, 1993
INVENTOR(S) : Uwe Herrmann, et al

It is certified that error appears in the above-indentified patent and that said Letters Patent is hereby corrected as shown below:

Col. 2, Line 40:   after "In the" and before "known" delete "1".

Claim 8, line 1:   after "claim" delete "4" and insert "7".

Signed and Sealed this

Twenty-seventh Day of September, 1994

Attest:

BRUCE LEHMAN

Attesting Officer

Commissioner of Patents and Trademarks